United States Patent
Malaquin et al.

(10) Patent No.: US 10,947,491 B2
(45) Date of Patent: Mar. 16, 2021

(54) PRINT HEAD OF A PRINTER, PRINTER AND PRINTING METHOD

(71) Applicants: CENTRE NATIONAL DE LA RECHERCHE SCIENTIFIQUE, Paris (FR); INSTITUT CURIE, Paris (FR); SORBONNE UNIVERSITE, Paris (FR)

(72) Inventors: Laurent Malaquin, Ayguesvives (FR); Jean Louis Viovy, Paris (FR); Sandrine Souleille, Escalquens (FR); Xavier Dollat, Roques sur Garonne (FR); Victor Fournie, Labège (FR)

(73) Assignees: CENTRE NATIONAL DE LA RECHERCHE SCIENTIFIQUE, Paris (FR); INSTITUT CURIE, Paris (FR); SORBONNE UNIVERSITE, Paris (FR)

( * ) Notice: Subject to any disclaimer, the term of this patent is extended or adjusted under 35 U.S.C. 154(b) by 0 days.

(21) Appl. No.: 16/635,126

(22) PCT Filed: Aug. 3, 2018

(86) PCT No.: PCT/EP2018/071189
§ 371 (c)(1),
(2) Date: Jan. 29, 2020

(87) PCT Pub. No.: WO2019/025615
PCT Pub. Date: Feb. 7, 2019

(65) Prior Publication Data
US 2020/0247046 A1    Aug. 6, 2020

(30) Foreign Application Priority Data

Aug. 3, 2017    (FR) ...................................... 1757496

(51) Int. Cl.
*B29C 64/209*    (2017.01)
*B33Y 30/00*    (2015.01)
(Continued)

(52) U.S. Cl.
CPC ........... *C12M 33/04* (2013.01); *B29C 64/106* (2017.08); *B29C 64/209* (2017.08); *B33Y 10/00* (2014.12);
(Continued)

(58) Field of Classification Search
CPC ...... B29C 64/209; B33Y 30/00; B41J 2/1433; B41J 2/2002; B41J 2/1411; B41J 2/1721; B41J 2202/12; C12M 33/04
See application file for complete search history.

(56) References Cited

U.S. PATENT DOCUMENTS

| | | | |
|---|---|---|---|
| 2004/0189750 A1* | 9/2004 | Miura | B41J 2/04586 347/52 |
| 2010/0091078 A1* | 4/2010 | Lee | H05K 3/125 347/102 |

(Continued)

FOREIGN PATENT DOCUMENTS

WO    2014/197999 A1    12/2014

OTHER PUBLICATIONS

Written Opinion of the International Searching Authority dated Oct. 10, 2018, issued in corresponding International Application No. PCT/EP2018/071189, filed Aug. 3, 2018, 8 pages.
(Continued)

*Primary Examiner* — Matthew Luu
*Assistant Examiner* — Kendrick X Liu
(74) *Attorney, Agent, or Firm* — Christensen O'Connor Johnson Kindness PLLC

(57) ABSTRACT

A microfluidic print head of a printer has a distal face, an injection channel, a suction channel, a groove, and a light
(Continued)

source or an optical waveguide. The injection channel is configured to inject an ink onto a substrate and leads onto the distal face by an injection opening The suction channel is configured to suck up the ink and leads onto the distal face by a suction opening. The groove is defined on the distal face and into which the suction opening leads.

20 Claims, 10 Drawing Sheets

(51) Int. Cl.
| | |
|---|---|
| *B41J 2/14* | (2006.01) |
| *B41J 2/17* | (2006.01) |
| *C12M 1/26* | (2006.01) |
| *B33Y 10/00* | (2015.01) |
| *B29C 64/106* | (2017.01) |
| *B41J 2/175* | (2006.01) |

(52) U.S. Cl.
CPC ............. *B33Y 30/00* (2014.12); *B41J 2/1433* (2013.01); *B41J 2/1721* (2013.01); *B41J 2/17523* (2013.01); *C12M 33/00* (2013.01); *B41J 2002/14411* (2013.01); *B41J 2202/12* (2013.01)

(56) References Cited

U.S. PATENT DOCUMENTS

| | | |
|---|---|---|
| 2015/0037445 A1 | 2/2015 | Murphy et al. |
| 2017/0210069 A1 | 7/2017 | Stubenruss |
| 2017/0274475 A1* | 9/2017 | Pan ...................... B23K 26/342 |
| 2020/0199514 A1* | 6/2020 | Hauser ................ A61L 27/3886 |

OTHER PUBLICATIONS

International Preliminary Report on Patentability dated Feb. 4, 2020, issued in corresponding International Application No. PCT/EP2018/071189, filed Aug. 3, 2018, 1 page.

International Search Report dated Oct. 10, 2018, issued in corresponding International Application No. PCT/EP2018/071189, filed Aug. 3, 2018, 7 pages.

Written Opinion of the International Searching Authority dated Oct. 10, 2018, issued in corresponding International Application No. PCT/EP2018/071189, filed Aug. 3, 2018, 9 pages.

Moon, S., et al "Layer by Layer Three-dimensional Tissue Epitaxy by Cell-Laden Hydrogel Droplets", Tissue Engineering Part C: METHODS, vol. 16, No. 1, Feb. 2010, pp. 157-166.

* cited by examiner

PRINT HEAD OF A PRINTER, PRINTER AND PRINTING METHOD

The invention relates to the field of bioprinting, and more specifically to printers.

Bioprinting enables considerable medical advances. Among these advances, can be mentioned the creation of implants or of living structures made of cells and extracellular matrix, as for example skin or bone structures.

Currently, bioprinting is primarily used for medical research. Bioprinting enables the creation of microenvironments of cell cultures and of living tissue models that are useful for the diagnosis and analysis of mechanisms that give rise to certain pathologies. Scientists are already using it, in particular to study the evolution of tumour cells or of stem cells. This enables them to better understand the evolution of cells, in particular cancer cells, to better cure cancers and to protect humanity from cancers.

It has been established that cancer cells, as an example among others, need a three-dimensional microenvironment that is spatially heterogeneous. The components of this microenvironment are physical (topology, mechanical properties, etc.), chemical (composition of the extracellular matrix, concentration of biochemical factors, etc.) and spatial (distribution of the various cell types that make up the tissue, etc.). In bioprinting, the physiological three-dimensional microenvironment is reconstructed to allow control of the cellular proliferation and differentiation processes, while also ensuring the long-term functionality of generated tissues.

Ultimately, the goal scientists are working towards is the creation of functional, biometric, implanted tissue models. For example, these can be "bioprinted" human organs for the purpose of regenerative medicine. These are functional tissues that mimic or not a pathology and that can be used for pharmaceutical or therapeutic applications.

Several technologies are currently used for bioprinting. However, these technologies all have disadvantages that are particularly limiting for scientists.

In the following description, the term "ink" is used to describe a photosensitive material, comprising a polymer or a hydrogel or a mixture of polymers and hydrogels, comprising or not living cells and comprising or not additional molecules such as proteins, DNA, acids, alkalis, sugars, growth factors, peptides, markers, charged particles, molecules and colloids.

A first technology is a microextrusion technique. This technique consists of using one or more print head(s). Each head permits depositing a hydrogel fibre generated by extrusion through a nozzle, this fibre having a diameter that varies based on the diameter of the nozzle. These fibres are successively juxtaposed and superposed so as to generate a three-dimensional structure. This hydrogel can be seeded or not with cells. In the case of one single material, the printing of the structures that serve as a culture support is generally followed by immersion in a suspension of cells that are deposited at the surface thereof. The inks are pushed through a micro syringe and deposited by means of a needle. This technology has multiple disadvantages. Firstly, the size of the needle determines the resolution of the achieved structures. The needles have a given diameter, generally of one hundred micrometres, and therefore enable material printing to a similar resolution, of approximately 100 μm. Moreover, the resolution in the extrusion axis of the fibres is hard to control and is generally greater than 100 μm, as it is not determined by the diameter of the nozzle but by flow control. This technology is faced with a significant problem, namely that to increase resolution, needles with smaller diameters increase the shear stress during the extrusion process, in turn harming the properties of the gels or a reducing the viability of the cells possibly present in the extruded material (in the ink). The shear stress that is exerted on the cells during the displacement thereof can be deleterious, i.e. increase apoptosis, in particular if the needle is too small and/or if the extrusion speed is excessive. Moreover, this technology involves relatively long printing times. It must be noted also, that the creation of heterogeneous structures, i.e. involving the successive use of different inks, can be laborious. The printing of multiple inks translates into the sequential use and the alignment of several extrusion heads each containing the inks to be printed. It is impossible to mix these materials during extrusion in order to adjust their relative concentrations. Moreover, the limited resolution of this approach (100 μm, i.e. ten times bigger than a cell), does not enable accurate control of the organisation of the printed structures.

A second technology is an inkjet technique. The inkjet technique consists of a print head that sprays micro-droplets of ink. This technique has a resolution of around fifty micrometres and involves significant precautions that must be taken to preserve cell viability during printing. Indeed, the devices used to generate micro-drops are based on thermal or piezoelectric effects that cause shear and compression stress, along with a significant temperature increase that can harm cell viability.

A third technology is a laser-assisted transfer printing technique. This technique consists of depositing a film of ink on a metallised slide. In this printing technique, a laser is directed by means of a mirror and focused by a lens before hitting the slide on the face opposite the face on which the ink is deposited. This technology achieves a precision of one micrometre. This laser-assisted printing technique has disadvantages. Among these disadvantages, the created constructions are unstable when it comes to creating three-dimensional structures, and in particular when hollow or solid structures with high aspect ratios are required, i.e. structures that have complex shapes. In addition, heterogeneous structures are particularly hard to create because of the necessity of sequentially using a different slide for each ink. In this technique, each slide comprises a type of cell. When a cell is hit by the laser, it is ejected and deposited on a substrate. In order to add a different cell and to create a heterogeneous structure, another slide has to be used, on which is deposited another type of cell, while ensuring that the slide in question is perfectly aligned. This is laborious and requires a level of accuracy that is difficult to achieve, because (repeated) slide manipulations are required. A heterogeneous structure is a structure made of different cells, of different extracellular matrixes and/or of different biomolecules.

It must furthermore be noted, that in order to produce a tissue, the heterogeneity of the tissue must be reproduced at the scale of the individual cell. This heterogeneity includes the type of cell and the spatial position thereof, the concentration of species and their spatial concentration, the type of extracellular matrix, the porosity thereof, the physiochemical and mechanical properties thereof, and the spatial distribution of these properties.

The invention aims at overcoming at least one of these disadvantages.

An aim of the invention is to propose a microfluid print head of a printer that can create heterogeneous structures while retaining a resolution at least less than 100 micrometres, preferably less than 50 micrometres and more preferably less than 20 micrometres.

Another aim is to provide a printer able to print, on request, a structure made of one or more type(s) of ink.

Another aim is to provide a printer wherein the ink flows can be controlled in real time to create a mixture with a carefully adjusted ink composition.

Another aim is to provide a printer wherein the quantities of ink used are minimised.

Another aim of the invention is to provide a printer that can print in the three spatial directions while retaining a resolution at least less than 100 micrometres, preferably less than 50 micrometres and more preferably less than 20 micrometres.

Another aim is to provide a printer that is able to print with various wavelengths, including UV, visible and infrared light.

Another aim is to provide a printer able to print at different resolutions.

Another aim is to provide a printer that can print at various resolutions in order to optimise printing speeds.

Another aim is to provide a printer able to print while using several types of ink.

Another aim is to provide a printer able to print while maintaining the structures immersed in a culture medium throughout the printing process.

To this end, the invention firstly provides a microfluid print head of a printer wherein the head comprises a distal face and:
- at least one first channel referred to as injection channel for injecting an ink onto a substrate, the injection channel leading onto the distal face through a first opening referred to as injection opening,
- at least one second channel referred to as suction channel for suctioning up the ink, among others, the suction channel leading onto the distal face through a second opening referred to as a suction opening,
- a groove defined on the distal face and wherein the suction opening leads,
- at least one light source or optical waveguide for transmitting the light emitted by a light source, and wherein the light source or optical waveguide is able to project a beam of light onto a lighting zone located on the distal face, the lighting zone in turn being able to project a beam of light from the distal face thereof.

Several additional features can be added, alone or as in combination:
- the print head comprises a body and an end-piece provided on the body, the end-piece comprising the injection opening, the suction opening, the groove and the lighting zone;
- the body comprises the injection channel, the suction channel and the light source or the optical waveguide, respectively located opposite the injection opening, the suction opening and the lighting zone;
- the end-piece is made of a transparent material, preferably a Polydimethylsiloxane elastomer;
- the depth of the groove extends along a longitudinal axis of the end-piece and the groove has a shape that surrounds the lighting zone;
- the groove extends over the circumference of the end-piece (24) according to an angular sector ranging from 180° to 340°, and preferably 320°;
- the groove has a radial width that is substantially constant and ranges from 20 to 500 µm, and preferably from 100 to 300 µm;
- an axial depth of the groove measured between the distal face and a deeper point located in the groove ranges from 20 to 500 µm and preferably from 100 to 300 µm;
- the depth of the groove is substantially constant;
- the lighting zone has a diameter ranging from five to five hundred micrometres;
- the injection opening and the suction opening have diameters ranging from twenty micrometres to one millimetre;
- the lighting zone comprises a platform protruding from the distal face, on a distance ranging from 50 to 500 µm, preferably 100 µm,
- the end-piece comprises an annular crown that extends on the perimeter of said nozzle, the crown protruding from the distal face,
- the end-piece comprises a front cavity arranged between the injection opening and the platform, and a rear cavity arranged between the platform and the suction opening,
- the groove has a variable axial depth,
- the crown comprises an annular edge extending the crown, said annular edge being oriented in the direction of the platform such that the annular edge partially overlaps with the suction opening and/or the injection opening.

Secondly, the invention provides a printer that comprises:
- at least one ink reservoir,
- at least one injection pump able to put the ink reservoir under pressure,
- a distributor fluidly connected to the ink reservoir, the distributor being able to control the flow rate of the ink collected from the ink reservoir,
- a robotic arm able to move or a robotic base able to move,
- at least one print head such as described above, mounted on the robotic arm when the printer comprises a robotic arm, or said at least one print head mounted on a fixed support of the printer when the printer comprises a robotic base, the at least one print head being fluidly connected to the distributor to supply ink to the at least one print head, the at least one print head being able to inject ink onto a substrate,
- suction means fluidly connected to the print head in order to suction ink injected by the print head,
- a suction reservoir fluidly connected to the suction means to store the suctioned ink,
- at least one light source able to polymerise the ink at the level of the print head if the print head does not comprise a light source,
- a connected computer unit that controls the injection pump, the distributor, the robotic arm or, depending on the case, the robotic base, the suction means and the light source.

Thirdly, the invention provides a printing method using a printer comprising:
- at least one ink reservoir,
- at least one injection pump able to put the ink reservoir under pressure,
- a distributor fluidly connected to the ink reservoir, the distributor being able to control the flow rate of the ink collected from the ink reservoir,
- a robotic arm able to move or at least one robotic base able to move,
- at least one print head such as described above, mounted on the robotic arm when the printer comprises a robotic arm, or on a fixed support of the printer when the printer comprises a robotic base, the at least one print head being fluidly connected to the distributor to supply the latter with ink, the at least one print head being able to inject ink onto a substrate, suction means fluidly connected to the print head in order to suction ink injected by the print head, a suction reservoir fluidly connected to the suction means to store the suctioned ink, at least one light source able to polymerise the ink at the level of the print head if the print head does not comprise a light source, a connected computer unit that controls the injection pump, the distributor, the robotic arm or, depending on the case, the robotic base, the suction means and the light source, wherein the method is implemented by means of a computer program in the computer unit, the method comprising:

a step of injecting at least one ink by means of the print head on an immersed substrate, a step of suctioning the ink through the print head, a step of polymerising the injected ink by means of the at least one light source, these steps being performed simultaneously during at least some of the printing time.

Several additional features can be added, alone or as a combination thereof:

the printing method comprises a step of moving the robotic arm in at least one spatial direction;

the printing method comprises a step of moving the robotic base in at least one spatial direction.

Other features and advantages of the invention are explained in the following description, with reference to the appended drawings, which are provided as examples, the invention not being limited thereto, wherein.

Figure 4A:
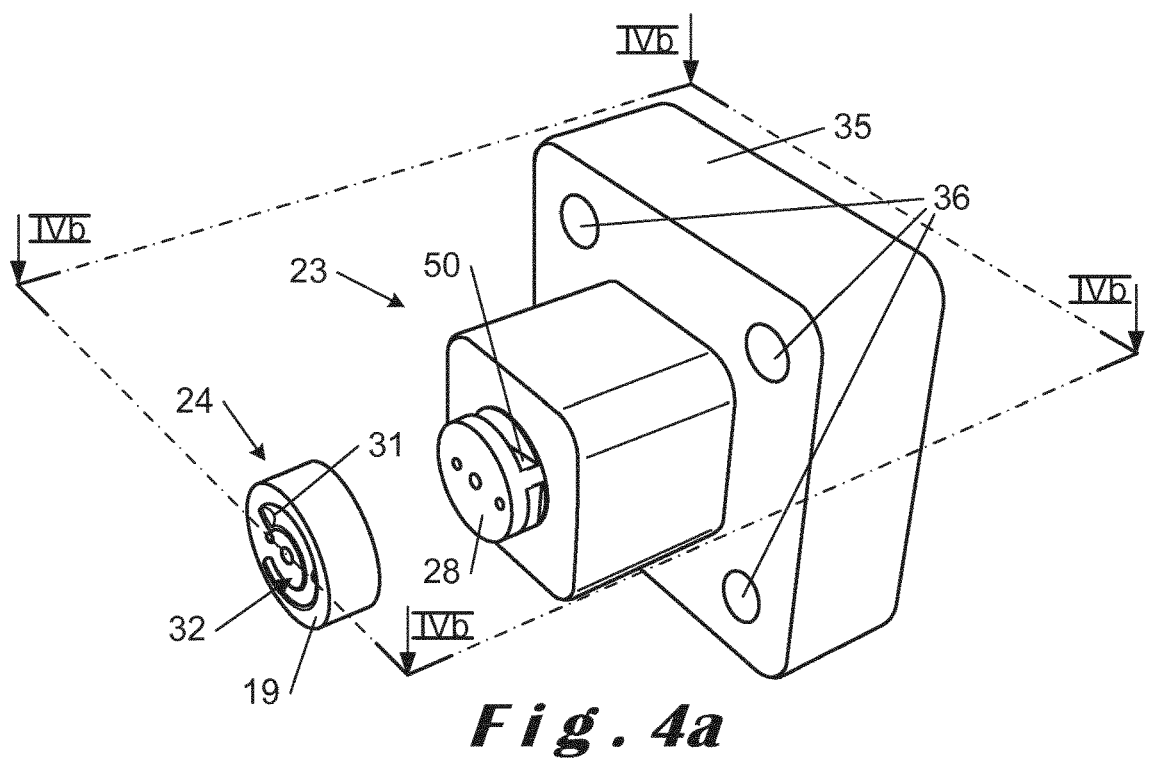
FIG. 4a is a perspective view of the end-piece and of a plate of the print head.
Figure 4B:
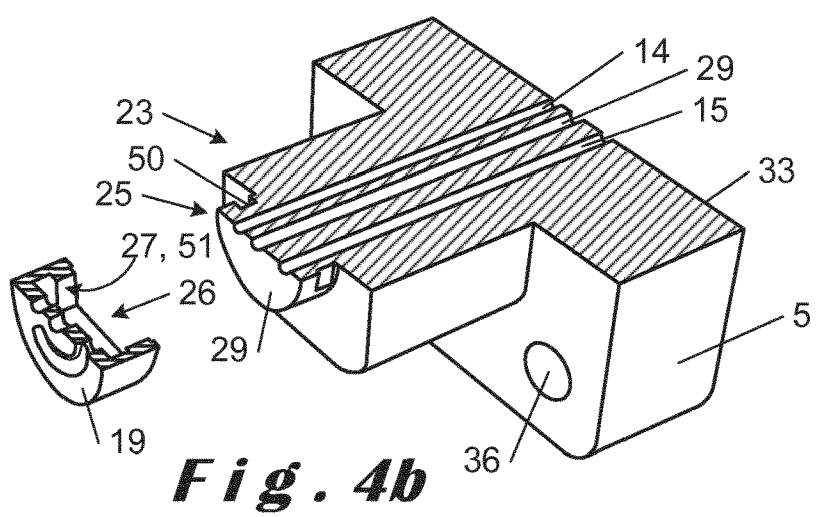
FIG. 4b is a cross-sectional view according to the three-dimensional plane IVb-IVb of FIG. 4a, FIG. 4c is a two-dimensional view of the end-piece according to one embodiment version.
Figure 4C:
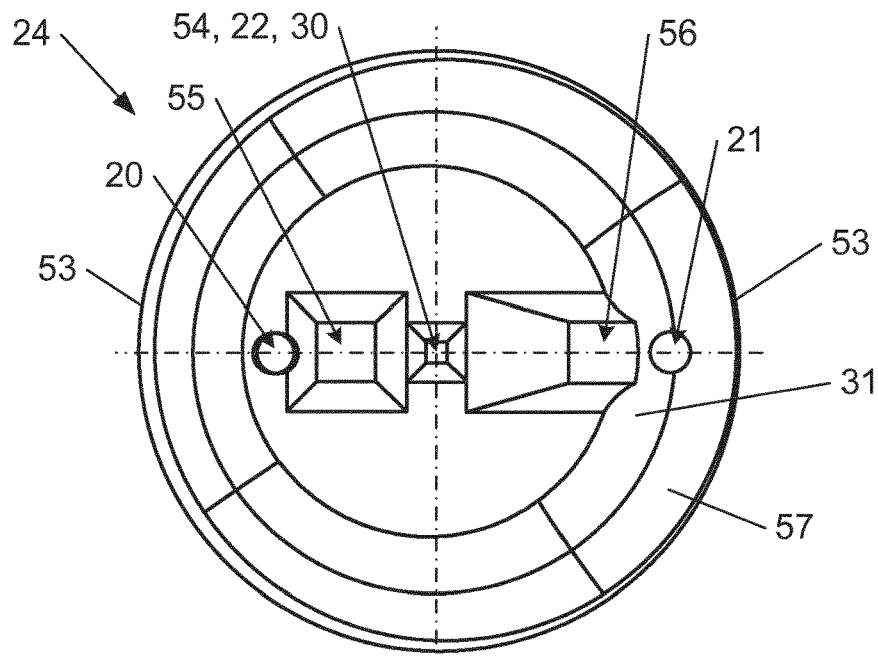
FIG. 4d is a perspective view of the end-piece of FIG. 4c.
FIG. 4e is a cross-sectional view according to the IVe-IVe plane of FIG. 4d.
Figure 4D:
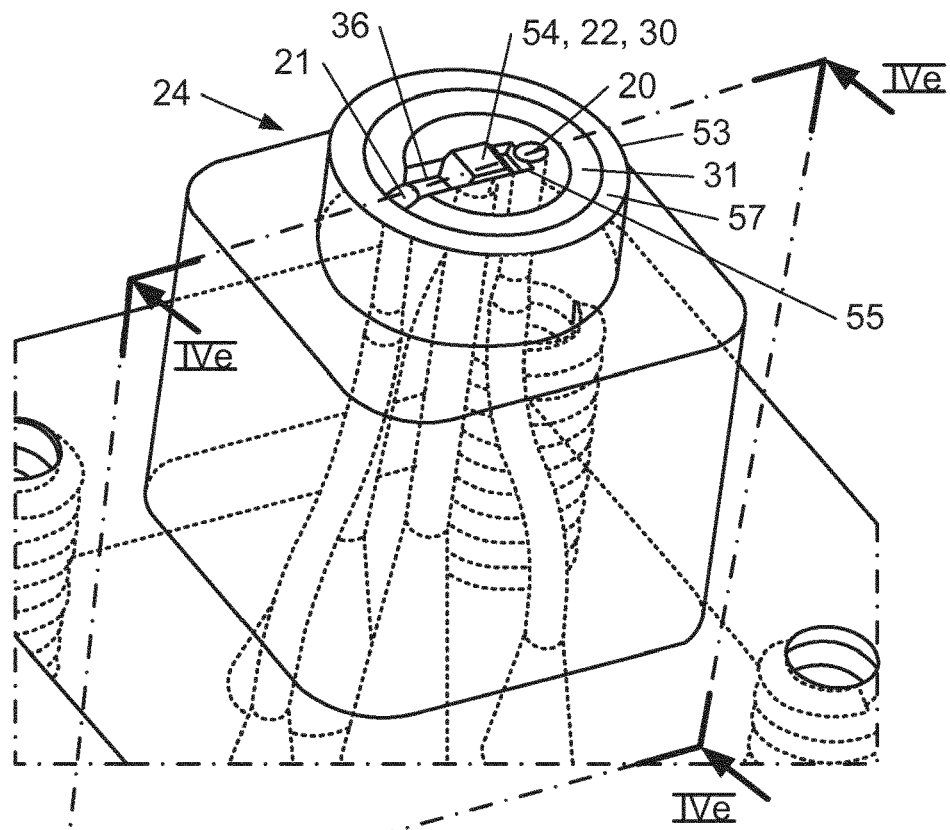
Figure 4E:
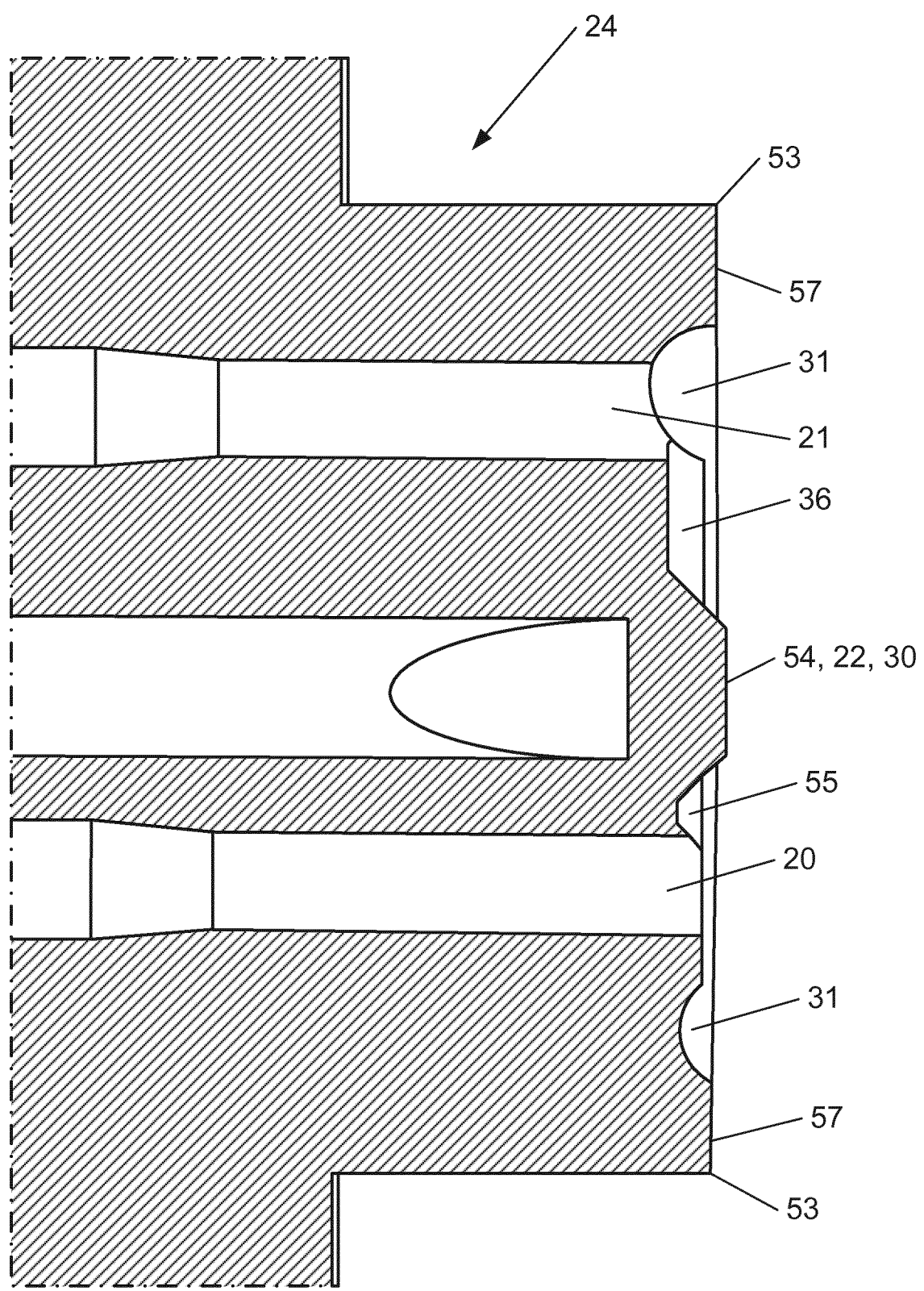
Figure 4F:
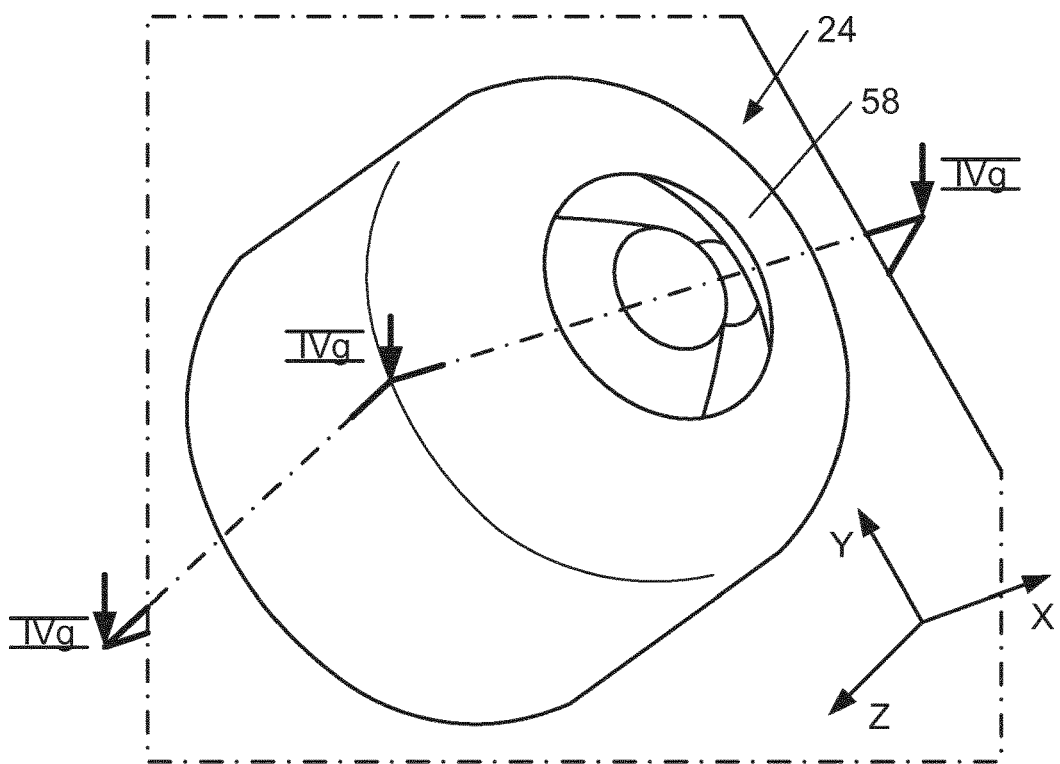
Figure 4G:
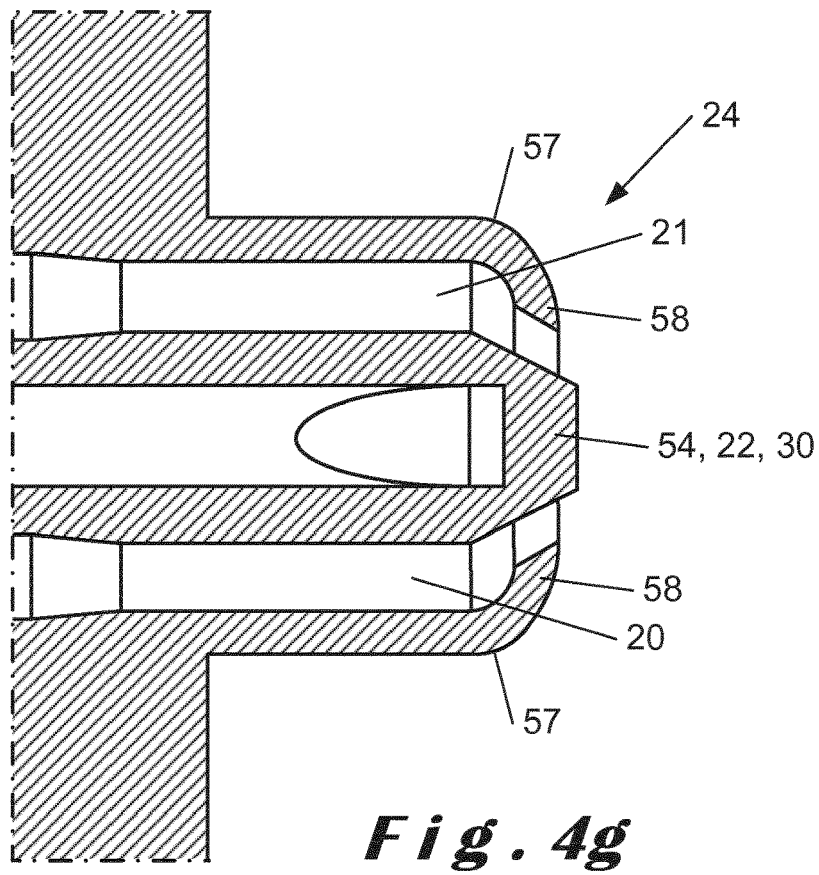
Figure 5:
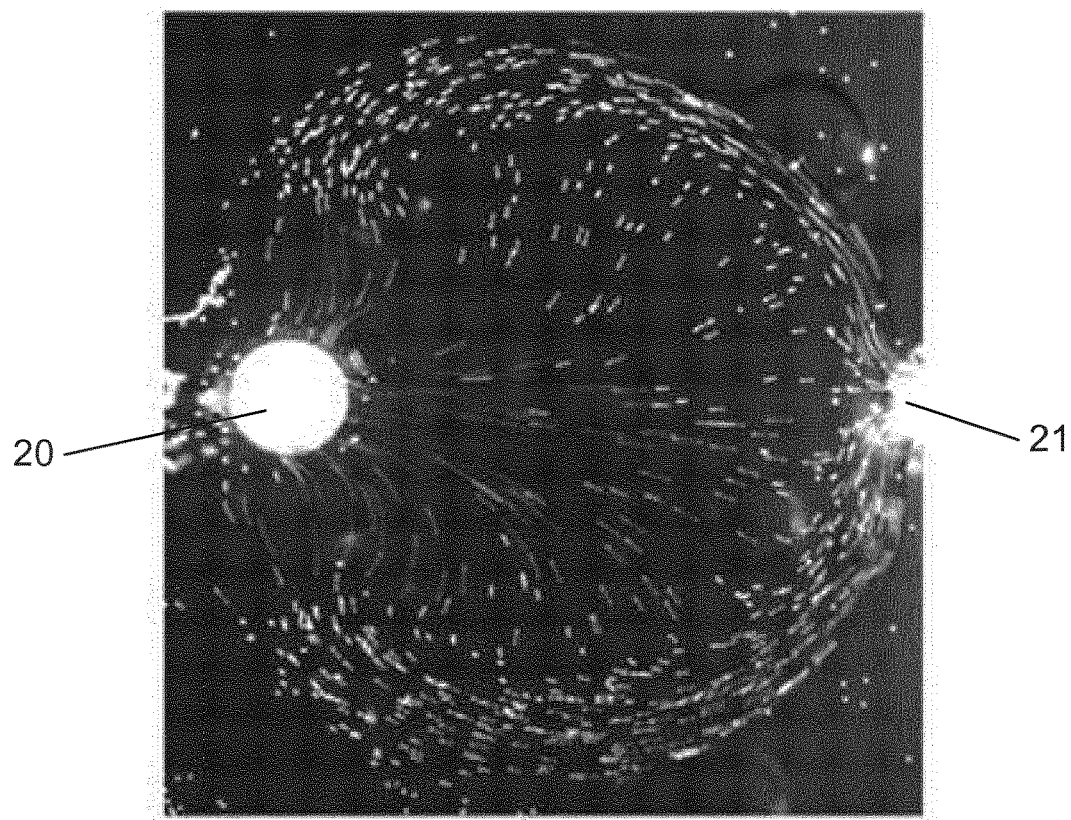
Figure 6:
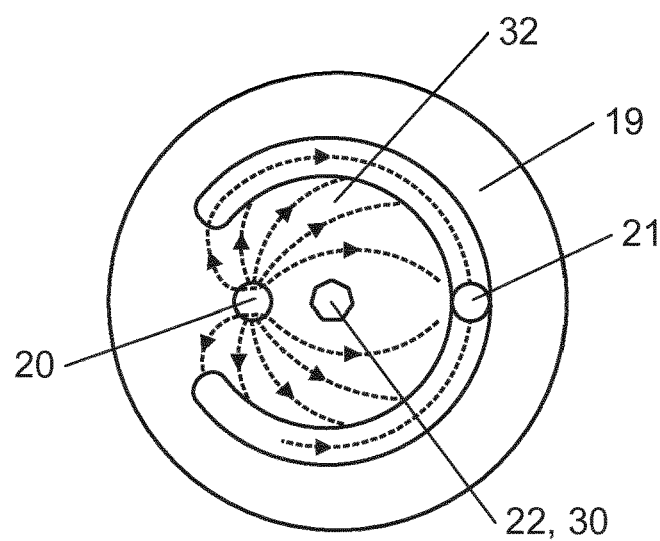
Figure 7:
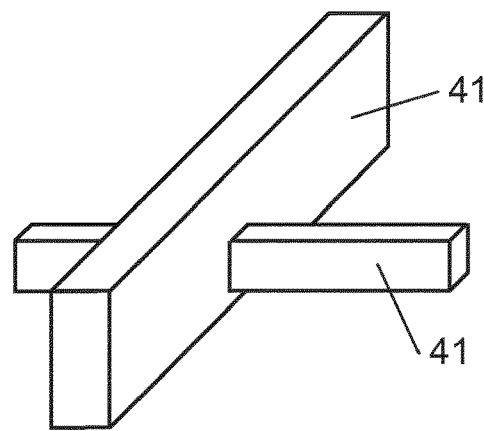
Figure 8:
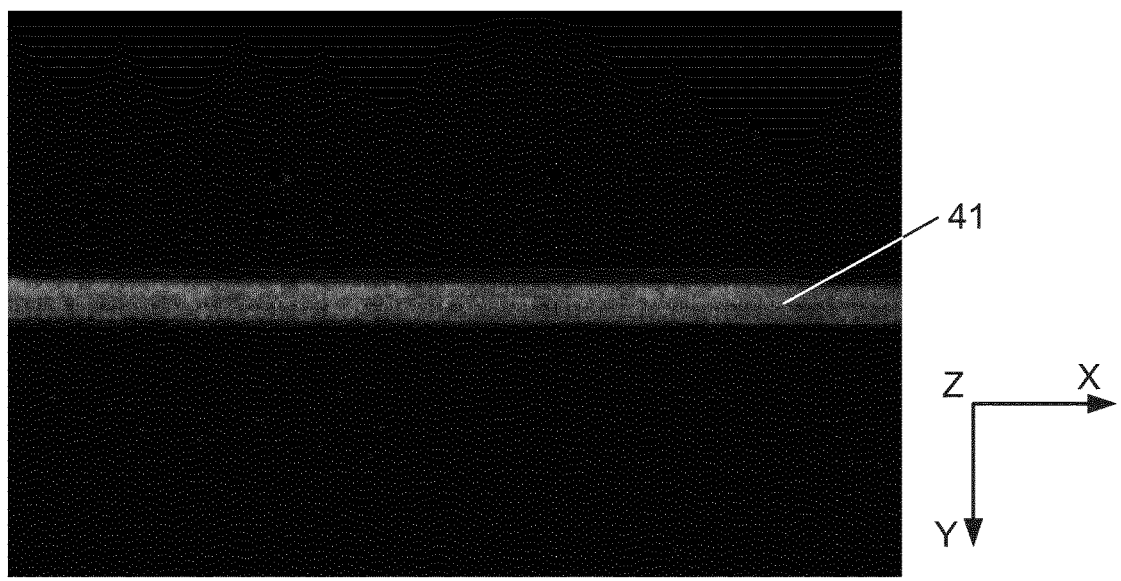
Figure 9:
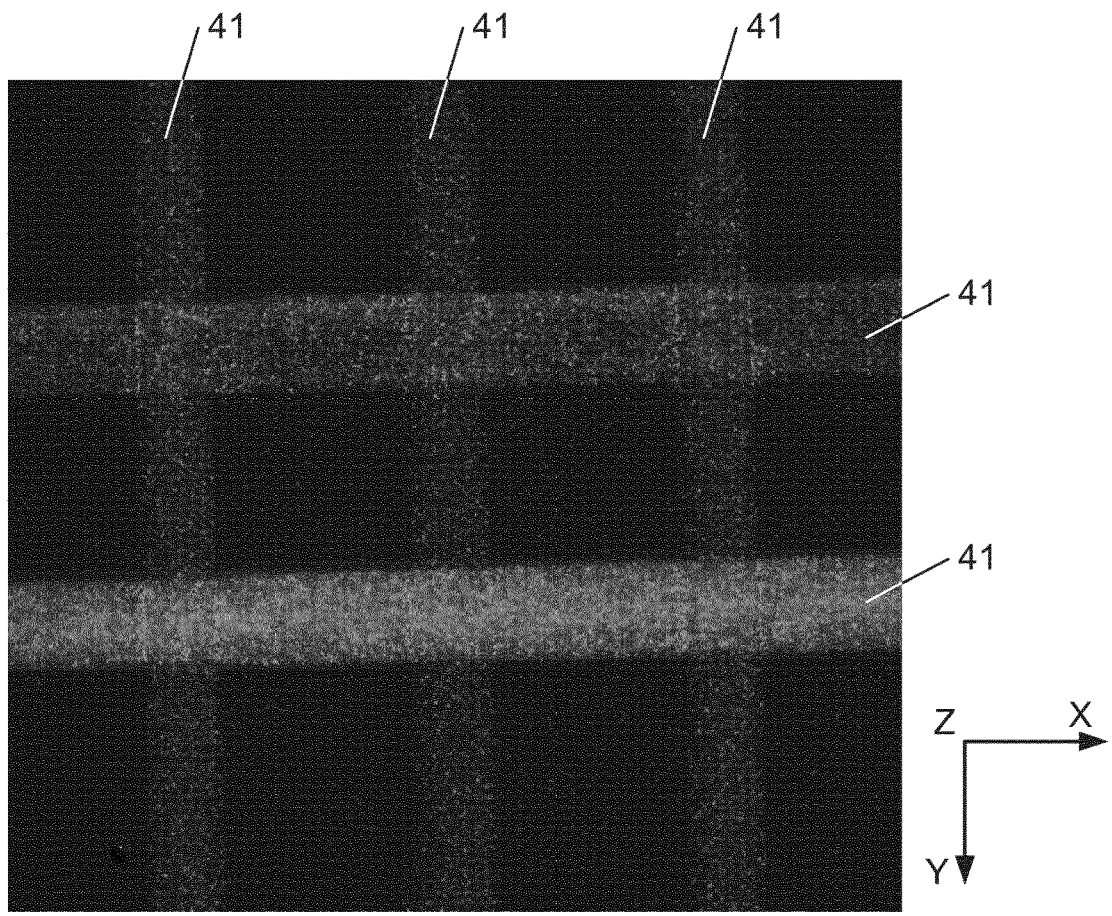
Figure 10:
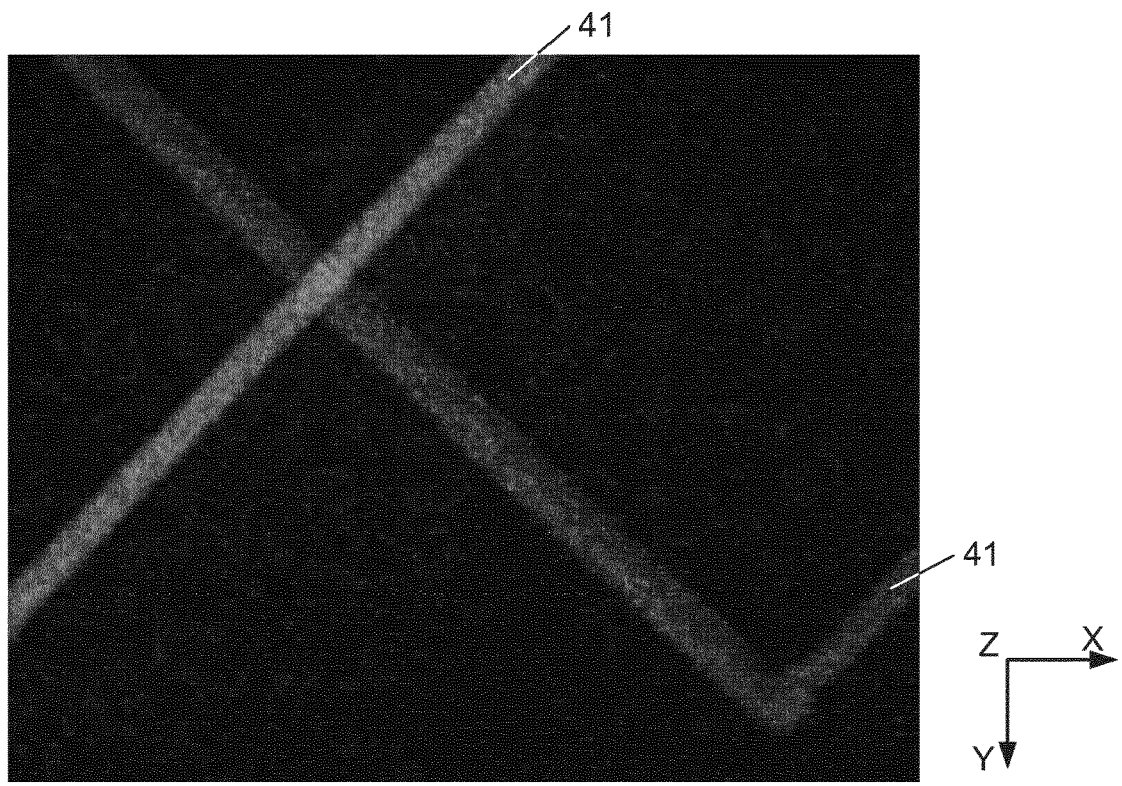
Figure 11:
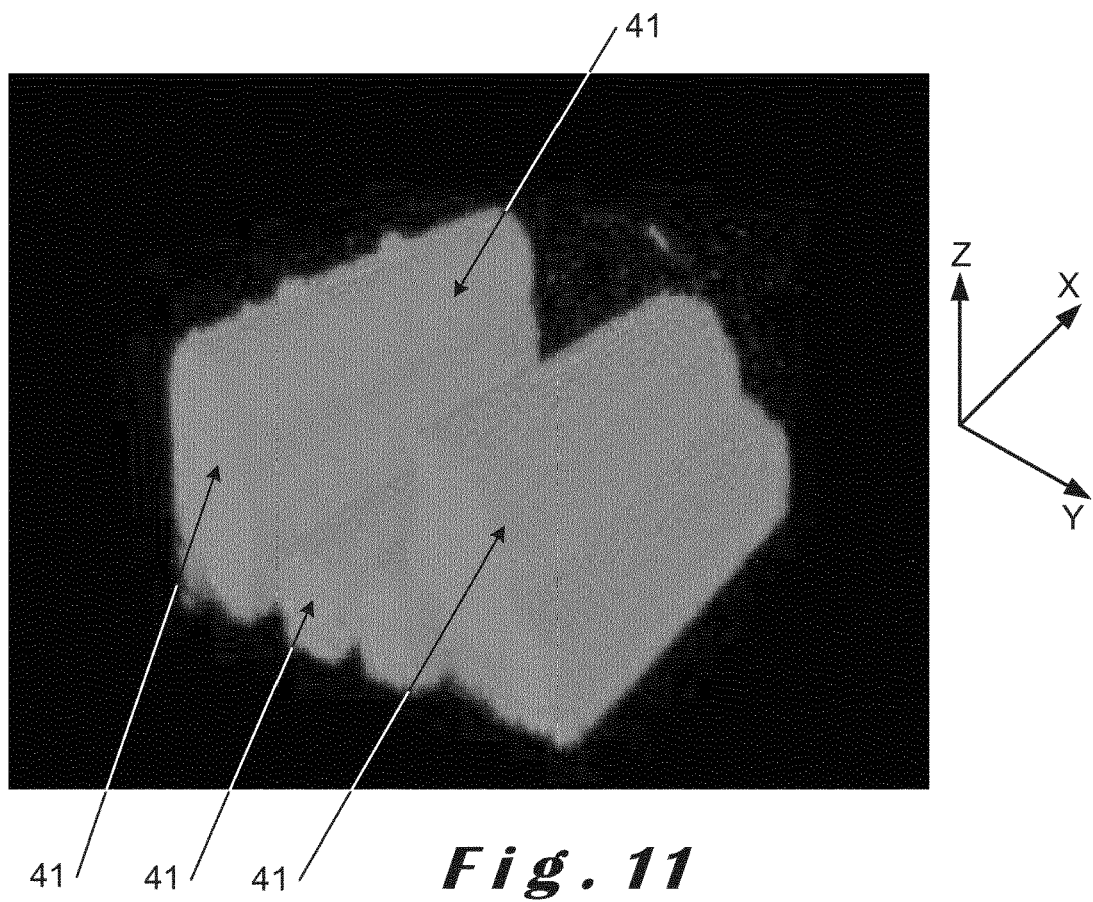
Figure 12:
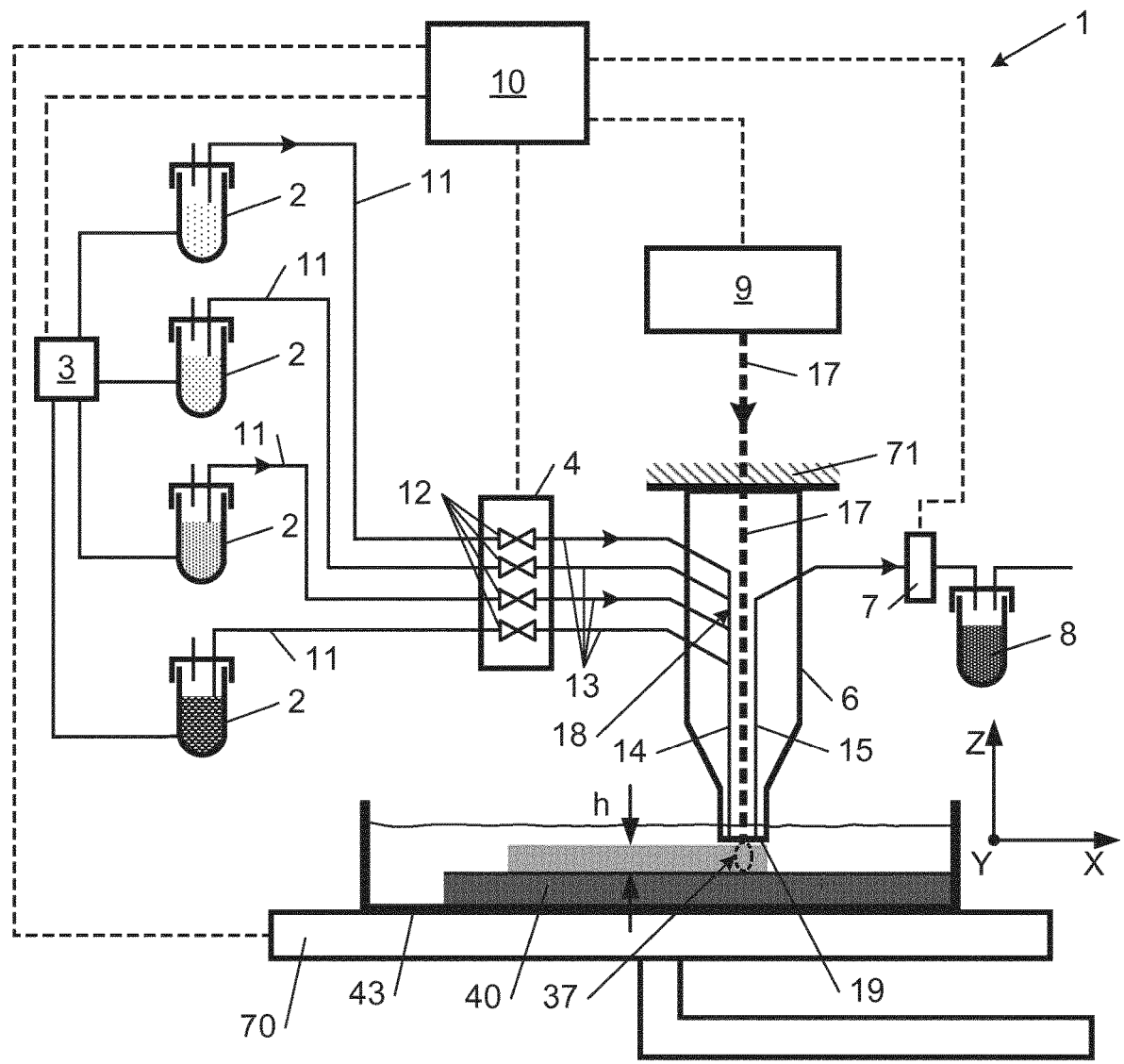
Figure 13:
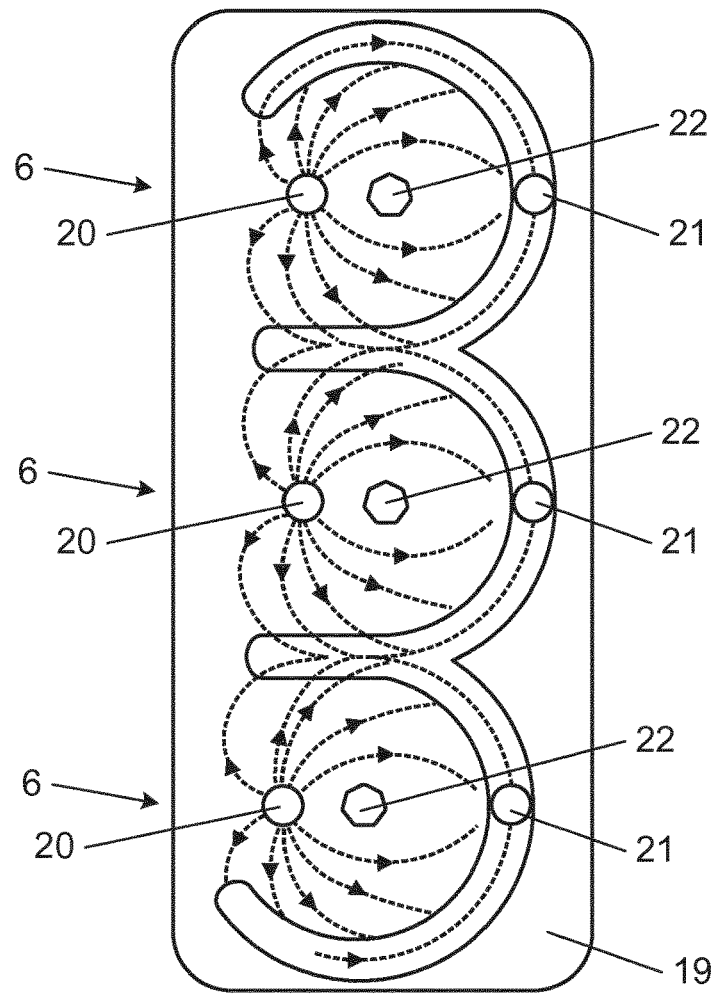
Figure 14:
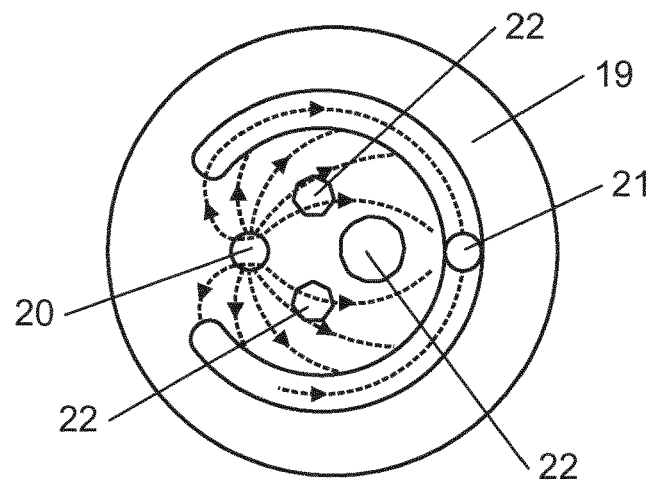

FIG. 4f is a perspective view of an end-piece according to another embodiment version, FIG. 4g is a cross-sectional view according to the IVg-IVg plane of FIG. 4f, FIG. 5 is a real image illustrating the motion of particles, FIG. 6 is a two-dimensional and schematic view of the end-piece, FIG. 7 is a schematic view of walls printed by the print head according to the invention, FIG. 8 is a top view of a real image showing a two-dimensional printed wall, FIG. 9 is a top view of a real image showing two-dimensional printed walls, FIG. 10 is a top view of another real image showing two-dimensional printed walls, FIG. 11 is another real image showing three-dimensional printed walls, FIG. 12 is a schematic view of the printer according to an embodiment version, FIG. 13 is a two-dimensional and schematic view of an embodiment version of the end-piece, FIG. 14 is a two-dimensional and schematic view of an embodiment version of the end-piece.

Figure 1:
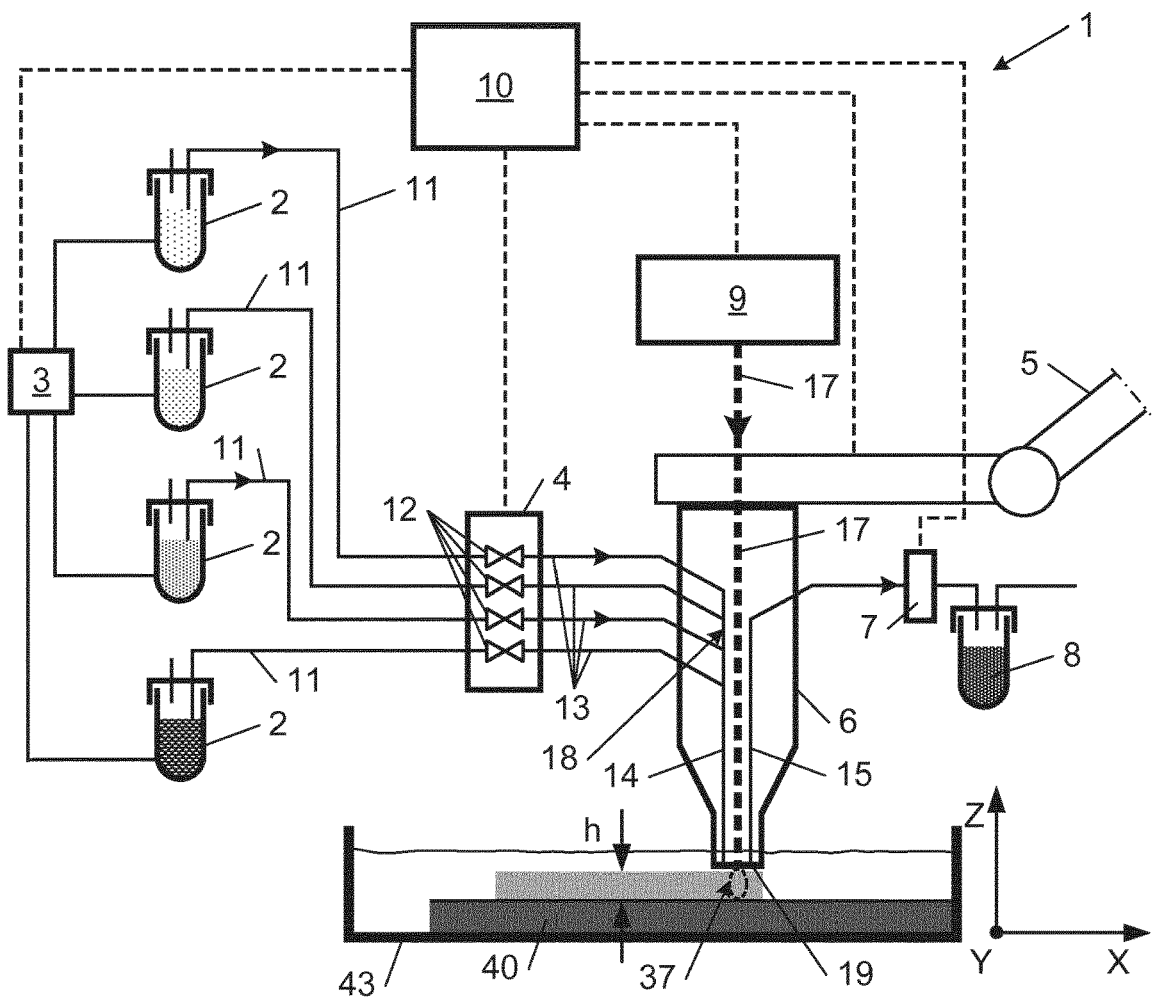
FIG. 1 is a schematic view of a printer according to the invention.

FIG. 1 is a schematic view of a printer 1.

The printer 1 comprises:
at least one ink reservoir 2,
at least one injection pump 3 able to put the ink reservoir 2 under pressure,
a distributor 4,
a robotic arm 5,
a print head 6,
suction means 7,
a suction reservoir 8,
at least one light source 9 that can be integrated or not in the print head 6, and
a computer unit 10.

An X, Y, Z trihedral is defined, the X axis of which represents a first horizontal displacement direction of the robotic arm 5, the axis Y, perpendicular to the axis X, representing a second horizontal displacement direction and the axis Z, perpendicular to the axes X and Y, representing a vertical displacement direction. The axes X, Y and Z define the planes XY, XZ and YZ.

In the embodiment shown in FIG. 1, the printer 1 comprises four ink reservoirs 2. Each reservoir 2 contains a different ink.

The number of inks and consequently the number of reservoirs 2 can be adapted to specific requirements, i.e. based on the heterogeneity of the structure that is to be printed.

Each reservoir 2 is fluidly connected to the distributor 4 by means of a supply channel 11.

The distributor 4 contains a plurality of valves 12, equal in number to that of the supply channels 11. Each valve 12 is able to open or close a supply channel 11. The distributor is able to open and close the supply channels 11 based on the printing needs. The valves 12 can be of the on/off type, i.e. they are, in a binary manner, either open or closed. These valves 12 can also be of the variable-opening type. In this case, they can be used to adjust the flow rate in the supply channels 11 to the user's preferences.

At the outlet of the distributor, each supply channel 11 is extended by a feed channel 13 fluidly connected to the print head 6 of the printer 1. In an embodiment that is not shown in the figures, the distributor 4 can be integrated in the print head 6.

The print head 6 is described as microfluid because of the dimensions, in particular, of the channels it contains, which over at least one portion of the path thereof have a dimension perpendicular to the axis, and preferably two dimensions perpendicular to the axis less than one millimetre, for example, approximately ten or a hundred micrometres. The dimensions are presented in further detail below.

The print head 6 comprises:
at least one first channel termed injection channel 14,
at least one second channel termed suction channel 15,
at least one light source 9 or optical waveguide 17 for transmitting the light emitted by a light source 9.

The suction means 7 enable control of the flow rate or the suction pressure in the suction channel 15.

In the embodiment shown in the figures, the print head 6 comprises an optical waveguide 17.

The feed channels 13 are fluidly connected to the injection channel 14 of the print head 6 at the level of a branched connection 18. The ink mixtures are thus prepared in the print head 6. However, the ink mixtures can be prepared at a different level. For example, it is possible for the branched connection 18 to be located outside of the print head 6.

Figure 2:
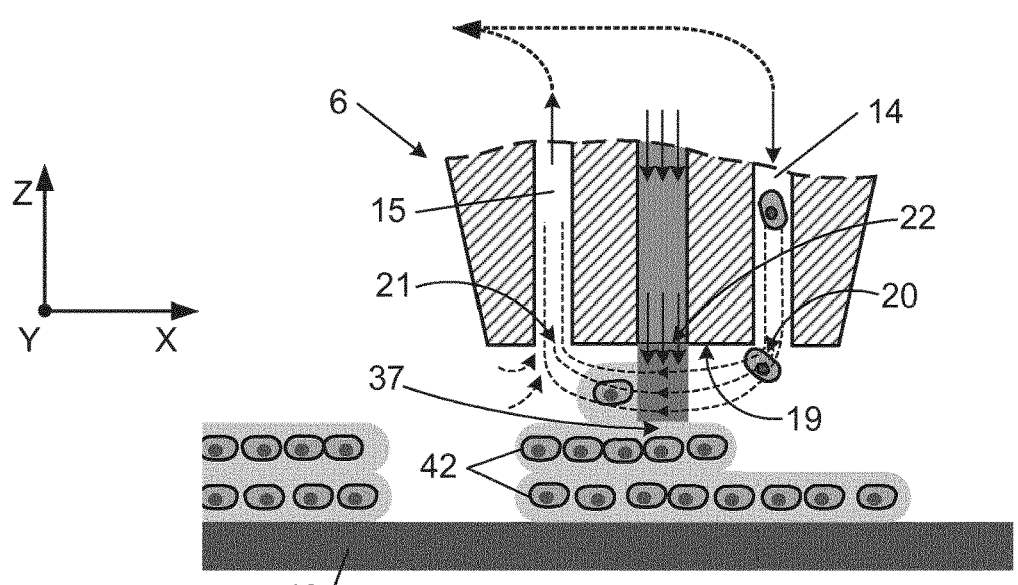
FIG. 2 is a schematic view of an end of a print head of the printer of FIG. 1.

With reference to FIG. 2, the injection channel 14 and the suction channel 15 open onto a distal face 19 of the print head. The distal face 19 is located at an end of the print head 6. The injection channel 14 and the suction channel 15 respectively open onto the distal face 19 through a first opening termed injection opening 20 and a second opening termed suction opening 21. The light source 9 is able to light a lighting zone 22 located on the distal face 19. The lighting zone 22 is a delimited zone preferably lit by a light source 9 for example able to generate a collimated light beam. A light source 9 is able to generate a beam of light, preferably coherent. Other beams can also be used. By way of example, light sources such as LED, laser diodes, CCD or VCSEL devices can be used. The lighting zone 22 is advantageously protected by means of a transparent material, contrary to the injection opening 20 and the suction opening 21, in order to protect the light source 9 from the ink that might damage it.

With reference to FIGS. 4a and 4b, the print head 6 comprises a body 23 and an end-piece 24. This is advantageously able to produce a print head 6 using two different materials, in particular in terms of the end-piece 24, which has specific features, as explained below.

According to one preferred embodiment, the end-piece 24 has a cylindrical shape with a diameter ranging from one hundred micrometres to five millimetres. Other shapes of the end-piece 24 are also possible as alternative versions.

Figure 3:
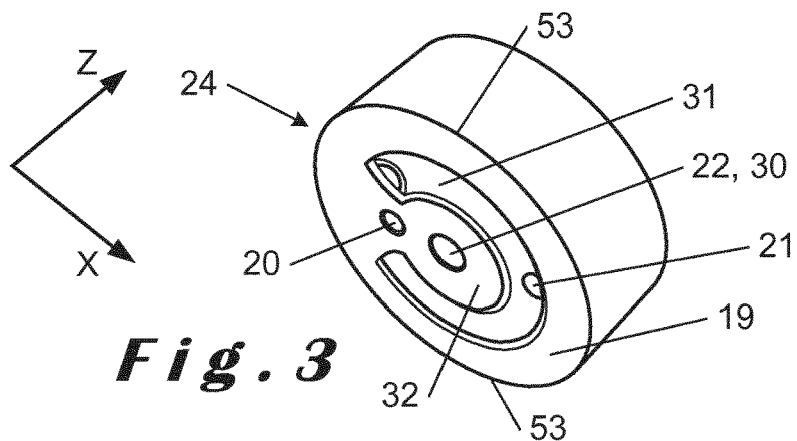
FIG. 3 is a perspective view of an end-piece of the print head.

According to a preferred embodiment, the end-piece 24 can be provided on the body and secured thereto. Various attachment means can be considered. In the embodiment shown, the body 23 comprises an end portion 25 provided with notches 50 while the end-piece 24 defines a hollow cavity 26, the internal walls 27 of which comprise pins 52 that can be inserted in the notches 50. The end-piece 24 is provided on and secured to the end portion 25 by means of the pins 51 housed in the notches 50. The end portion 25 is provided with an intermediate face 28 on which open the injection channel 14, the suction channel 15 and a third channel termed optical channel 29. The end-piece 24 comprises the distal face 19, the injection opening 20, the suction opening 21 and the lighting zone 22. In FIGS. 3, 4a and 4b, the lighting zone 22 is in the form of a third opening termed optical opening 20 provided on either side of said end-piece 24 and opening onto the distal face 19, like the injection opening 20 and the suction opening 21. When the end-piece 24 is mounted on the end portion 24 of the body 23, the injection opening 20, the suction opening 21 and the optical opening 30 are positioned respectively opposite the injection channel 14, the suction channel 15 and the optical channel 29 of the body 23.

In an alternative embodiment, the end-piece is transparent. In this case, the end-piece 24 does not comprise an optical opening.

The print head 4 is made of one single unit. The print head 4 can comprise more than two different materials. In the case of a print head 4 made of one single unit, the latter is advantageously transparent to allow light to shine through.

Advantageously, the distal face 19 is provided with an axial groove 31. The groove 31 comprises, at least partially, the suction opening 21. In the embodiment shown in the figures, the suction opening 21 is encompassed in the groove 31. In other words, the suction opening 21 is fully contained within the groove 31. In a preferred embodiment, the groove 31 is in the shape of a circular arc around a centre and extending over the circumference of the end-piece 24 along an angular sector ranging from 180° to 340°, preferably substantially equal to 320°. Thus, the groove 31 is not closed. Experiments have shown that an angle of 320° advantageously is able to channel, in the suction channel, all of the injected ink. According to embodiments not shown in the figures, the shape of the groove 31 is not limited to a circular arc. It can, for example, be in the shape of an elliptic arc. It can also have another shape able to, preferably, to surround the lighting zone 22.

The groove 31 has a radial width (along a radial axis X of the end-piece) that is substantially constant. The radial width preferably ranges from 20 to 500 µm, and preferably from 150 to 250 µm.

The groove 31 has an axial depth (along the axis Z) measured between the distal face 19 and a deeper point located in the groove 31 preferably ranging from 20 to 500 µm and preferably from 150 to 250 µm. Preferably, the groove 31 also has a substantially constant depth and/or a substantially constant cross-section.

Such a depth and such a radial width of the groove 31 enable it to achieve optimal retrieval of the injected ink.

The groove 31 defines a central zone 32. The injection opening 20 is advantageously located in the central zone 32. Thus, when ink is expelled from the print head 6 through the injection opening 20, the portion of ink that is not polymerised is advantageously channelled through the groove 31, and then suctioned by the suction opening 21. The motion of the ink is described below.

The groove 31 can, in cross-section (according to the cross-sectional plane XZ), have the shape of a square, an ellipse, a pyramid or any other form, but it is preferably cylindrical.

The lighting zone 22 is advantageously located between the injection opening 20 and the suction opening 21. More accurately, the openings 20, 21 and the optical opening are aligned. In other words, each opening comprises a centre (not shown in the figures) such that a line (not shown) intersects substantially with each of these centres. However, it is possible that these centres are not aligned, for instance when the print head 6 comprises several injection, suction and optical openings 20, 21, 30. This alternative version, not shown in the figures, is described below.

The suction channel 15 is fluidly connected to the suction means 7 and to the suction reservoir 8. A suction means can, for example, be a suction pump.

In the embodiment shown in FIGS. 1 to 4, the light source 9 used is a coherent light source 9, for example, a laser. The power of the laser 9 ranges from 0.1 mW to 160 mW, and preferably from 1 mW to 10 mW. The power of the emitted laser 9 corresponding to the quantity of energy per surface unit is 0.8 mW for an exposed circular surface area with a diameter of 20 µm. The lighting ranges from $0.3 \times 10^6$ Wm$^{-2}$ to $500 \times 10^6$ Wm$^{-2}$ and preferably from $1 \times 10^6$ to $75 \times 10^6$ Wm$^{-2}$. The wavelength ranges from 265 nm to the infrared spectrum, and preferably from 365 nm to 750 nm. The laser 9 is located outside the print head 6, as shown schematically in FIG. 1. The light source 9 can be a laser diode, a LED or a VCSEL. Other tools can also be used. Preferably, the lighting zone 22 (and consequently the light beam) has a diameter ranging from five to five hundred micrometres.

In this embodiment, the optical channel 29 provided in the print head 6 extends from a top surface 33 thereof to the intermediate face 28. The print head 6 comprises an optical waveguide 17 inserted in the optical channel 29 and able to guide the coherent beam of the laser 9 to the optical opening 30. With reference to FIG. 4, a lower end (not shown in the figures) of the optical waveguide 17 is located at the level of the intermediate face 28. Advantageously, the optical waveguide 17 does not extend to the optical opening 30. The lower end of the optical waveguide comprises a lens, for example a spherical lens, able to both to protect the optical waveguide 17 and to achieve a better light beam. The optical waveguide 17 is, for example, an optical fibre. In an alternative embodiment, it is possible that the optical waveguide 17 is not provided with a lens.

In an alternative embodiment not shown in the figures, the optical opening 30 can be provided with an additional lens, depending on the need.

As mentioned above, the printer 1 comprises a computer unit 10 that is able to coordinate all the different elements that it comprises. The computer unit 10 can be a computer, a microprocessor, or more generally any automated means for controlling electronic, optical, mechanical and/or fluidic operations. Thus, the computer unit 10 can be connected by wires or by a wireless system to the injection pump 3, the distributor 4, the robotic arm 5, the light source 9 and the suction pump 7. These connections are schematically shown in dotted lines in FIG. 1. The computer unit comprises a processor in which is implemented a computer program, in order to implement a printing method.

The term "pump" is not at all limiting, it can be any means able to compress or transport a fluid, or to create a low pressure (suction).

The body of the print head 6 comprises a plate 35 provided with a plurality of attachment holes 36. The holes 36 are intended to house attachment screws (not shown). The plate 35 is advantageously attached on the robotic arm. The robotic arm 5 can move in the three spatial directions. It enables the print head 6 to construct three-dimensional structures.

The body is advantageously made of polymer. The body 23 is, for example, made by machining. Other materials can be used.

According to a preferred embodiment, the end-piece 24 is made of a polymer, preferably a transparent polymer. Preferably also, this transparent polymer is an elastomer, for example Polydimethylsiloxane. It is made by moulding using a micro-machined mould (not shown). The print head can also be made of this material. The print head and the end-piece 24 can thus be made of the same material or of different materials.

The material with which the end-piece 24 is manufactured has a specific importance, as this is the material in contact with a polymerisation zone 37. The polymerisation zone 37 is a zone where the three-dimensional structure is created.

Advantageously, the material(s) used to manufacture the print head is/are:
  inert with respect to the polymerisation reaction,
  preferably but not necessarily transparent in order to enable the light beams emitted by the light source to shine through the material at the level of the lighting zone,
  preferably porous to gases, in particular to oxygen, in order to locally inhibit the polymerisation reaction on a reduced thickness of approximately one micrometre, and to prevent the polymerised material from sticking to the end-piece 24 during the printing process.

The end-piece 24 can be made of an elastomer deformable polymer, a rigid polymer or a metal, for instance Polydimethylsiloxane (PDMS), which has the advantage of being inert, transparent, deformable and, because of the porosity thereof to oxygen, it prevents polymerisation and the ink from sticking to the surface. In the case of the end-piece 24 not being made of a transparent material (as is the case in the embodiment shown in the figures), it is preferable to create an optical opening 30 at the level of the lighting zone 22 (as mentioned above), and to insert a transparent window therein in order to protect the light source. In this case, the transparent window can be a flat slide or a lens, for example a spherical lens to achieve a light beam that is preferably collimated, as explained above.

It must be noted, that the print head can be made entirely of the same material.

As mentioned above, the light source 9 can be integrated in, or separate from, the print head 6. In the latter case, the print head 6 comprises an optical waveguide 17 such as an optical fibre, to direct the light beams through the print head 6, all the way to the lighting zone 22. In order to eliminate the optical waveguide 17, an embodiment alternative can consist of positioning the light source 9 close to the distal face 19.

The injection opening 20 and the suction opening 21 have diameters ranging from twenty micrometres to one millimetre. The diameters of the injection channel 14 and of the suction channel 15 also range from twenty micrometres to one millimetre. These dimensions are advantageous as they protect the cells 42 from shear stress. Alternatively, the injection opening 20 and the suction opening 21 can have a cross-section with a square or rectangular shape, or any other shape. A preferred shape is however circular.

The injection pressure in the injection channel 14 preferably ranges from zero to one bar. This pressure is achieved by pressurising the reservoirs 2 with the injection pump 3. The suction pressure is of between minus one bar (depression) and zero bar. This suction pressure is obtained by means of the suction pump 7. Advantageously, the suction (depression) flow rate in absolute value is greater than the injection flow rate in absolute value, to prevent the contamination of the medium surrounding the head between the injection opening 20 and the suction opening 21, and to enhance the retrieval of inks injected by the injection opening 20.

The print head 6 has a speed of displacement along the axis X and along the axis Y that can reach one centimetre per second. The printing process is generally conducted along the axis X and along the axis Y, with simultaneous or isolated motion along these axes. The head can also move along the axis X, the axis Y and the axis Z, simultaneously, or perform a motion in the plane XY, followed by a motion according to the axis Z and inversely. The speed of the print head 6 along the axis Z can also reach ten centimetres per second.

A distance separating the print head 6 from a substrate 40 ranges from 10 µm to 800 µm. It must be noted, that below 20 µm, fluid circulation is difficult, and beyond 400 µm, the ink retrieval efficiency by suction reduces, inducing a risk of contamination of the surrounding medium. In a preferred manner, this distance ranges from 40 µm to 200 µm.

In what follows, the operation of the printer is described. As explained above, the print head 6 is moved by a robotic arm 5 controlled by the computer unit 10. A three-dimensional structure is created by means of a computer-assisted design tool and imported in the computer unit 10. The structure can, for example, be contained in a computer file. The structure can be heterogeneous (several inks) or simple (one single ink). The heterogeneity of the structure can also be obtained by injecting locally different inks, or by changing the wavelength and/or the intensity of the light source during the printing process.

The substrate 40 intended to support the structure is immersed in a fluid, preferably an aqueous solution that constitutes the polymerisation zone, all of which is contained in a Petri dish 43, for example. In other embodiments, the polymerisation zone can contain another liquid, for example an oil. In a preferred embodiment, the print head 6 is positioned such that the distal face 19 of the end-piece 24 is immersed in the water and hydrogel mixture.

The printing process starts when the computer unit 10 instructs the distributor 4 to open at least one opening valve 12. The corresponding inks are thus routed towards the print head 6. The ink(s) pass through the injection channel 14 and is/are ejected onto the print head 6 through the injection opening 20. The inks are ejected in all directions that are available to them. In parallel, the suction pump 7 is activated. The depression in the suction channel 15 is greater in absolute value, to the injection pressure in the injection channel 14. The inks ejected by the injection channel are directed towards the suction channel 15. The portion of the inks directed towards the suction channel 15 taking the shortest path available to them by passing under the lighting zone 22 is polymerised. The activation of the light source or sources generates the localised polymerisation of the inks, and the head is then moved. The light source is activated during the displacement, when the position of the head with respect to the sample reaches the zone to be polymerised. This polymerised ink attaches to the substrate 40, arranged beforehand opposite the distal face 19 of the print head 6. Simultaneously, another portion of the ejected ink is lost. This lost ink is channelled through the groove 31 and suctioned by the suction channel 15 through the suction opening 21. This ink is not polymerised as it bypasses the lighting zone 22.

It must be noted, that the suction flow rate is more important than the injection flow rate and, consequently, all of the injected ink is suctioned at the same time as the surrounding medium.

With reference to FIG. 5, fluorescent microparticles of ten micrometres were used to represent the ink flows. In this experiment, the injection pressure is of sixty millibar and the suction pressure is of ninety millibar. The mixture of water and hydrogel is respectively made in the proportion of twenty-five and seventy-five percent.

The structure of the end-piece 24, in particular thanks to the groove wherein the suction opening 21 is contained, advantageously is able to channel the ink, as seen in FIGS. 5 and 6. In FIG. 6 in particular, the motion of the ink is schematised by lines of flow arrows. As can be seen, almost all of the ink is channelled by the groove and suctioned. This mechanism is able to avoid the contamination of the surrounding medium and favours the renewal or the change of ink at the level of the polymerisation zone.

FIG. 4c shows an alternative embodiment of the print head. In this embodiment, the axial depth of the groove 31 varies. More specifically, the axial depth of the groove 31 varies with the distance to the suction opening 21. This increases the microfluidic resistance in the groove 31, enabling more ink to pass under the optical opening 30. The printing process is therefore more efficient.

In this embodiment, the lighting zone 22 comprises a platform 54. The platform 54 protrudes from the distal face 19 of the end-piece according to the axis Z. The height of the platform 54, along the axis Z, ranges from 50 to 500 μm, and is preferably 100 μm. A height of 100 μm achieves a good compromise between the suction of the material and the displacement speed of the print head. The platform 54 is able to move the end-piece away from the polymerisation zone 37 such that the peripheral edges 53 of the end-piece 24 do not come into contact with the polymerised ink. The platform 54 advantageously has a truncated pyramidal shape. Other shapes can be used, such as a cube, for example. However, a preferred embodiment comprises a platform in the shape of a truncated pyramid. Indeed, studies relating to flows around the platform 54 conducted by the applicant show that the use of a truncated pyramid advantageously avoids the presence of slow flow zones that can cause contaminations during ink changes.

In this embodiment, the end-piece 24 comprises a front cavity 55 arranged between the injection opening 20 and the platform 54. The end-piece 24 comprises a rear cavity 56 arranged between the platform 54 and the suction opening 21. The front and rear cavities 55, 56 have a substantially pyramidal shape. They are provided inside the end-piece along the axis Z. They advantageously create a fluidic space between the injection opening 20 and the platform 54 on the one hand, and between the platform 54 and the suction opening 21, on the other hand. This reduces micro fluid resistance, favouring the flow under the platform 54 and improving the renewal of ink. Cavities in the shape of truncated pyramids advantageously avoid sudden variations of height in said cavities. Other shapes can be used, such as semi-cylindrical cavities, for example. Indeed, sudden changes of the height inside the cavity would negatively impact the ink flow.

In this embodiment, the end-piece comprises a crown 57. The crown 57 is annular around the axis Z. It extends over the perimeter of the end-piece 24. The crown 57 protrudes from the distal face. The crown 57 does not protrude from the platform 54 along the axis z. In other words, the platform extends, at most, at the level of the platform 54 along the axis Z.

The end-piece 24 can be provided with the crown 57 and/or the platform 54 and/or the front cavity 55 and/or the rear cavity 56 and/or the variable-depth groove 31.

In an alternative embodiment shown in FIGS. 4f and 4g, the crown 57 comprises an annular edge 58. The annular edge 58 extends the crown 57 in the direction of the platform 54, i.e. along the axis X and the axis Y. Thus, the annular edge 58 overlaps partially with the suction opening 21 and the injection opening 20. Indeed, the head is positioned at a given distance from the substrate so as to have a confinement zone that enables good suction of the ink by the suction opening. By moving the head away from the substrate, the confinement zone is compromised, as is the suction of ink, thereby harming the printing process. The annular edge 58 is able to reproduce a confinement zone and to achieve proper suction, with the result that it is possible to move the print head away from the substrate to print higher structures, along the axis Z, and/or to increase the printing speed (displacement along the axes X and/or Y).

As mentioned above, the ink is polymerised by passing in front of the lighting zone 22 following the lateral dimensions (X, Y) defined by the shape of the beam. The thickness of the polymerised structure is defined by geometrical confinement by the distance from the distal face to the substrate 40 or to a structure printed beforehand. The ink is then reticulated on the substrate 40 or on a structure printed beforehand. The distal face 19 of the print head 6 is positioned at a given distance h from the substrate 40 or from a structure printed beforehand. This distance corresponds to the maximal height of a layer that the print head 6 can print during lighting. The X, Y resolution of printed structures is defined mainly by the optical properties of the light beam, inducing polymerisation and guaranteeing a given accuracy for layer thicknesses ranging from 0 to h. For example, when a structure with a height of six hundred micrometres on a given length is required, and when the printing capacity of the print head 6 is of two hundred micrometres in height with acceptable accuracy, the distal face 19 will initially be located at a distance of two hundred micrometres. The ink is polymerised by creating a first level of the structure measuring two hundred micrometres in height, and by moving laterally the robotic arm 5 in the required plane (X, Y) to create the required structure. Once the given length is reached, the robotic arm 5 is moved along the axis Z by a distance of two hundred micrometres and back tracks on the path thereof to build a second level, and so on until it reaches a height of six hundred micrometres, in this case three successive levels.

A schematic example of walls 41 intersecting with one another is represented in FIG. 7. In this figure, the intersecting walls 41 have different heights. FIG. 7 schematically shows that this method and this printer 1 are able to stack structures made of ink at the level of the intersection. Experiments conducted by the claimant show that stacks of structures are better achieved with a collimated light source that is able to increase the value h, i.e. maintaining the polymerisation accuracy over greater polymerisation thicknesses. The use of a focused beam is possible, but a collimated light beam is preferred.

The printer described above is able to create complex structures having discontinuities, different heights, wall intersections and stacks. It is able to create complex structures with hollow cavities. It offers great freedom of creation to scientists wishing to reproduce a cell growth environment.

A method for implementing the printer comprises:
- a step of injecting of one or more inks on an immersed substrate, the injection being done through the injection channel 14,
- a step of suctioning the ink or inks through the suction channel 15,
- a step of polymerising the injected ink(s).

These steps can be partially simultaneous, and are preferably simultaneous for some of the printing duration. They can also preferably be conducted at the same time as the print head 6 moves in space along one direction, or simultaneously along several directions (X, Y, Z). During the printing process, an end of the print head is immersed in the polymerisation zone 37.

The printer 1 described above has numerous advantages, among which:
- it offers the possibility of creating heterogeneous structures with a resolution at least less than 20 micrometres thanks to the accuracy of the light beam, the diameter of which is sufficiently reduced to achieve high resolution values,
- it is able to accurately control the composition of the mixture of inks used,
- the ink flows can be controlled in time and in space,
- the quantity of ink used is reduced,
- it can print in the three spatial directions, with a resolution of one micrometre,
- it can print at different wavelengths sequentially and/or simultaneously,
- it can print at different resolutions.

In an alternative embodiment (not shown) of the print head, it can comprise a plurality of injection channels, suction channels and lighting zones.

In another embodiment shown in FIG. 13, the printer can be provided with several print heads 6 and with several lighting zones 22. The wavelength and the diameter of the light sources can vary from one print head to another.

In another embodiment shown in FIG. 14, the print head 6 comprises several lighting zones 22. In this embodiment, the print head comprises three lighting zones with a wavelength and a diameter that can vary with respect to one another.

In another embodiment shown in FIG. 14, the print head 6 comprises an annular groove 31 that extends over the entire periphery of the print head, as well as a plurality of lighting zones 22. The lighting zones can have a wavelength and a diameter that vary from one lighting zone to another.

In an embodiment alternative not shown in the figures, the print head comprises an injection channel and two suction channels. Advantageously, the groove is annular. Tests conducted by the applicant show that such a print head is advantageous because the retrieval of ink through the suction opening is efficient.

In another embodiment (not shown) the print head is fixed and the Petri dish 43 is mounted on a robotic base controlled by the computer unit 10. In this embodiment, the print head is mounted on a fixed support, and only the base is in motion to form the structures that are to be printed. In this alternative embodiment, the print head 6 does not move, and the previously described steps of the process are performed at the same time as the robotic base moves.

The following description relates to several tests conducted in a laboratory.

These experiments were achieved with a printing process in a synthetic PEG DA (Poly(ethylene glycol) diacrylate) hydrogel. The printing process was performed on a glass slide functionalised with MAPTMS (Amino Propyl Tri Methoxy Silane) immersed in synthetic hydrogel.

Test 1 (FIG. 8): Hydrogel Structure Printed on a Glass Substrate

Ink: 50% PEG DA (Mw 700) 50% water 0.0075% of Irgacure 819 2% of fluorescent particles (diameter 300 nm)
Distance separating the distal face from the substrate: 60 μm
Injection pressure: 100 mbar
Suction pressure: −150 mbar
Speed along the X axis: 0.1 mm/s
Power of the laser: 4 mW
Resolution: 20 μm (width according to the axis Y)
Wavelength: 405 nm
In test 1, a horizontal line with a height of 60 μm is drawn.

Test 2 (FIG. 9): Hydrogel Structure Printed on a Glass Substrate

Ink: 50% PEG DA (Mw 700) 50% water 0.0075% of Irgacure 819 2% of fluorescent particles (diameter 300 nm)
Distance separating the distal face from the substrate: 60 μm, 120 μm, 140 μm.
Injection pressure: 100 mbar
Suction pressure: −150 mbar
Speed along the X axis: 0.1 mm/is
Power of the laser: 4 mW
Resolution: 50 μm (width according to the axis Y)
Wavelength: 405 nm
In this test 2, three vertical lines are drawn with a distance separating the distal face from the substrate of 60 μm.
Then, the distal face is positioned at a distance of 120 μm. A first horizontal line is drawn.
The distal face is then positioned at a distance of 140 μm. A second horizontal line is drawn.

This example shows that it is possible to stack layers with variable thicknesses on top of one another. Indeed, the results achieved are particularly promising and show that created structures are stable.

Indeed, at the intersection between the first horizontal line and any one of the vertical lines, the stacking of a first level and of a second level is achieved, and the structure is stable.

The same observation can be made in terms of the second horizontal line.

Test 3 (FIG. 10): Hydrogel Structure Printed on a Glass Substrate

Ink: 50% PEG DA (Mw 700) 50% water 0.0075% of Irgacure 819 2% of fluorescent particles (diameter 300 nm)

Distance separating the distal face from the substrate: 60 µm

Injection pressure: 100 mbar
Suction pressure: −150 mbar
Speed along the X axis: 0.1 mm/s
Power of the laser: 2 mW
Resolution: 20 µm (width in the plane XY)

In this test 3, the distance separating the distal face from the substrate is of 60 µm. A first oblique line is drawn, the length thereof is 1 mm and the width thereof is 30 µm.

The distance separating the distal face from the substrate is then increased by 40 µm, bringing it to 100 µm. A second oblique line with a height of 100 µm is drawn, with a length of 1 mm and a width of 40 µm.

The width increases with the distance from the lighting zone to the substrate. Light beams emitted by the lighting zone cannot be perfectly collimated, and therefore show a slight divergence.

Test 3 shows that it is possible, on the one hand, to draw oblique lines and that these structures are stable when they are stacked on one another, as is visible at the level of the intersection of these two lines.

Test 4 (FIG. 11): Hydrogel Structure Printed on a Glass Substrate

Ink: 50% PEG DA (Mw 700) 50% water 0.0075% of Irgacure 819 1% of fluorescent particles (diameter 300 nm)

Distance separating the distal face from the substrate: 60 µm

Injection pressure: 100 mbar
Suction pressure: −150 mbar
Speed along the X axis: 0.1 mm/s
Power of the laser: 10 mW
Resolution: 100 µm (width in the plane XY)

Test 4 was conducted with a distance separating the distal face from the substrate of 170 µm. Four adjacent lines are drawn on a length of 1 mm and with a width of 100 µm.

The height of the distal face is increased by 100 µm, bringing it to 270 µm, and two lines are drawn only on the side. (1 mm in length and 100 µm in width).

Then, the distance is once again increased by 150 µm, bringing it to 420 µm and two lines are drawn only on the side. (1 mm in length and 50 µm in width).

The invention claimed is:

1. A microfluidic print head of a printer, the microfluidic print head comprising:
    a distal face;
    at least one injection channel configured to inject an ink onto a substrate, the injection channel leading onto the distal face through an injection opening;
    at least one suction channel configured to suction up the ink, the suction channel leading onto the distal face through a suction opening;
    a groove defined on the distal face where the suction opening leads; and
    at least one light source or optical waveguide,
    wherein the at least one light source or optical waveguide is configured to project a beam of light onto a lighting zone located on the distal face, the lighting zone being configured to project the beam of light from the distal face.

2. The microfluidic print head according to claim 1, further comprising a body and an end-piece provided on the body, the end-piece comprising the injection opening, the suction opening, the groove, and the lighting zone.

3. The microfluidic print head according to claim 2, wherein the body comprises the injection channel, the suction channel, and the light source or the optical waveguide, respectively located opposite the injection opening, the suction opening, and the lighting zone.

4. The microfluidic print head according to claim 2, wherein the end-piece is made of a transparent material.

5. The microfluidic print head according to claim 2, wherein the groove extends in depth along a longitudinal axis of the end-piece, and has a shape surrounding the lighting zone.

6. The microfluidic print head according to claim 2, wherein the groove extends over a circumference of the end-piece according to an angular sector ranging from 180° to 340°.

7. The microfluidic print head according to claim 2, wherein the end-piece comprises an annular crown extending over a perimeter of the end-piece, the annular crown protruding from the distal face.

8. The microfluidic print head according to claim 7, wherein the end-piece comprises a front cavity arranged between the injection opening and the platform, and a rear cavity arranged between the platform and the suction opening.

9. The microfluidic print head according to claim 7, wherein the annular crown comprises an annular edge extending the annular crown, the annular edge being oriented in a direction of the platform such that the annular edge partially overlaps with at least one of the suction opening or the injection opening.

10. The microfluidic print head according to claim 1, wherein the groove has a radial width that is substantially constant and ranges from 20 µm to 500 µm.

11. The microfluidic print head according to claim 1, wherein an axial depth of the groove measured between the distal face and a deeper point located in the groove ranges from 20 µm to 500 µm.

12. The microfluidic print head according to claim 11, wherein the axial depth of the groove is substantially constant.

13. The microfluidic print head according to claim 1, wherein the lighting zone has a diameter ranging from 5 µm to 500 µm.

14. The microfluidic print head according to claim 1, wherein the injection opening and the suction opening have diameters ranging from twenty micrometres and one millimetre 20 µm to 1 mm.

15. The microfluidic print head according to claim 1, wherein the lighting zone comprises a platform protruding from the distal face by a distance ranging from 50 µm to 500 µm.

16. The microfluidic print head according to claim 1, wherein the groove has a variable axial depth.

17. A printer, comprising:
at least one ink reservoir;
at least one injection pump configured to pressurize the ink reservoir;
a distributor fluidly connected to the ink reservoir, the distributor being configured to control a flow rate of an ink collected from the ink reservoir;
a robotic arm configured to move or a robotic base configured to move;
at least one microfluidic print head according to claim 1 mounted on the robotic arm when the printer comprises the robotic arm, or on a fixed support of the printer when the printer comprises the robotic base, the at least one microfluidic print head being fluidly connected to the distributor and configured to supply the distributor with the ink, the at least one microfluidic print head being configured to inject the ink onto a substrate;
a suction pump fluidly connected to the microfluidic print head in order to suck the ink injected by the microfluidic print head,
a suction reservoir fluidly connected to the suction pump to store the suctioned ink,
at least one light source configured to polymerize the ink at a level of the microfluidic print head if the microfluidic print head does not comprise another light source,
a connected computer unit configured to control the injection pump, the distributor, the robotic arm or the robotic base, the suction pump and the at least one light source.

18. A method for printing with a printer having
at least one ink reservoir;
at least one injection pump configured to pressurize the at least one ink reservoir;
a distributor fluidly connected to the at least one ink reservoir, the distributor being configured to control a flow rate of an ink collected from the at least one ink reservoir;
a robotic arm configured to move or a robotic base configured to move;
at least one microfluidic print head according to claim 1, mounted on the robotic arm when the printer comprises the robotic arm, mounted on a fixed support of the printer when the printer comprises the robotic base, the at least one microfluidic print head being fluidly connected to the distributor to supply ink to the at least one microfluidic print head, the at least one microfluidic print head being configured to inject the ink onto a substrate,
a suction pump fluidly connected to the microfluidic print head in order to suck the ink injected by the microfluidic print head;
a suction reservoir fluidly connected to the suction pump to store the suctioned ink;
at least one light source configured to polymerize the ink at a level of the microfluidic print head if the microfluidic print head does not comprise another light source;
a connected computer unit configured to control the injection pump, the distributor, the robotic arm or the robotic base, the suction pump, and the at least one light source,
wherein the method is implemented by a computer program in the connected computer unit, the method comprising:
injecting the ink with the microfluidic print head on an immersed substrate;
suctioning the ink through the microfluidic print head; and
polymerizing the injected ink by the at least one light source,
wherein injecting, suctioning, and polymerizing are performed simultaneously during at least some of a printing time.

19. The method according to claim 18, further comprising moving the robotic arm in at least one spatial direction.

20. The method according to claim 18, further comprising moving the robotic base in at least one spatial direction.

* * * * *

UNITED STATES PATENT AND TRADEMARK OFFICE
CERTIFICATE OF CORRECTION

PATENT NO. : 10,947,491 B2
APPLICATION NO. : 16/635126
DATED : March 16, 2021
INVENTOR(S) : L. Malaquin et al.

It is certified that error appears in the above-identified patent and that said Letters Patent is hereby corrected as shown below:

On the Title Page

| Column | Line | |
|---|---|---|
| Pg. 2/Abstract Item (57) | 3 | change "opening The" to -- opening. The -- |

In the Claims

| Column | Line | |
|---|---|---|
| 16 | 62, 63 | change "from twenty micrometers and 1 millimeter 20" to -- from 20 -- |

Signed and Sealed this
Third Day of August, 2021

Drew Hirshfeld
*Performing the Functions and Duties of the
Under Secretary of Commerce for Intellectual Property and
Director of the United States Patent and Trademark Office*